(12) United States Patent
Wilhelm et al.

(10) Patent No.: US 7,593,158 B2
(45) Date of Patent: Sep. 22, 2009

(54) METHOD AND APPARATUS FOR THE EXAMINATION OF SPECIMENS

(75) Inventors: Stefan Wilhelm, Jena (DE); Eva Simbürger, Potsdam (DE); Michael Kempe, Jena (DE)

(73) Assignee: Carl Zeiss Micro Imaging GmbH, Jena (DE)

( * ) Notice: Subject to any disclaimer, the term of this patent is extended or adjusted under 35 U.S.C. 154(b) by 92 days.

(21) Appl. No.: 11/330,384

(22) Filed: Jan. 12, 2006

(65) Prior Publication Data

US 2007/0133086 A1  Jun. 14, 2007

(30) Foreign Application Priority Data

Dec. 8, 2005 (DE) .................. 10 2005 059 338

(51) Int. Cl.
  *G02B 21/06* (2006.01)
(52) U.S. Cl. .................. 359/385; 250/459.1; 359/900
(58) Field of Classification Search .................. None
  See application file for complete search history.

(56) References Cited

U.S. PATENT DOCUMENTS

| | | | |
|---|---|---|---|
| 5,105,304 A | 4/1992 | Tanaka et al. |
| 5,504,575 A | 4/1996 | Stafford |
| 5,751,417 A | 5/1998 | Uhl |
| 6,300,639 B1 | 10/2001 | Wiederhoeft |
| 6,377,344 B2 | 4/2002 | Schoeppe |
| 6,396,053 B1 | 5/2002 | Yokoi |
| 6,611,643 B2 | 8/2003 | Birk et al. |
| 6,633,381 B2 | 10/2003 | Uhl |
| 6,654,166 B2 | 11/2003 | Birk et al. |
| 6,796,699 B2 | 9/2004 | Birk et al. |
| 6,823,079 B1 | 11/2004 | Winterot et al. |
| 6,858,852 B2 | 2/2005 | Wolleschensky et al. |
| 6,888,674 B1 | 5/2005 | Birk et al. |
| 7,009,763 B1 | 3/2006 | Wolleschensky |
| 7,212,338 B2 | 5/2007 | Weyh et al. |
| 7,304,733 B2 | 12/2007 | Neher et al. |
| 2002/0030811 A1 | 3/2002 | Schindler |
| 2002/0109840 A1 | 8/2002 | Wolleschensky et al. |
| 2003/0021020 A1 | 1/2003 | Engelhardt et al. |

(Continued)

FOREIGN PATENT DOCUMENTS

DE  1915102  10/1970

(Continued)

*Primary Examiner*—Lee Fineman
(74) *Attorney, Agent, or Firm*—Jacobson Holman PLLC

(57) ABSTRACT

A method in which specimens are examined using a microscope. For an illuminated specimen, spatially coherent light with at least one continuous wavelength range or a continuously tunable wavelength range is generated, and one or more wavelengths or wavelength ranges in the illumination light are selected in dependence on the prespecified method of examination. The specimen is then illuminated with the illumination light with the selected wavelengths or wavelength ranges, the illumination light and the emission light coming from the specimen are then subsequently separated, whereby the back radiated illumination light is suppressed in the detection beam before the detection and the emission light is detected. In such a method, the selection of the wavelengths or the wavelength ranges of the illumination light is tuned by means of the separation of the detection light and the illumination light and the suppression of the illumination light in such a manner that a prespecified control variable (R) is optimized.

17 Claims, 11 Drawing Sheets

U.S. PATENT DOCUMENTS

| | | |
|---|---|---|
| 2003/0151741 A1 | 8/2003 | Wolleschensky et al. |
| 2004/0159797 A1 | 8/2004 | Wolleschensky |
| 2004/0218174 A1 | 11/2004 | Natori |
| 2005/0045812 A1 | 3/2005 | Birk et al. |
| 2005/0046836 A1* | 3/2005 | Olschewski ................. 356/318 |

FOREIGN PATENT DOCUMENTS

| | | |
|---|---|---|
| DE | 19829944 A1 | 1/2000 |
| DE | 19835070 | 2/2000 |
| DE | 19835072 A1 | 2/2000 |
| DE | 19916749 B4 | 10/2000 |
| DE | 10137158 A1 | 2/2003 |
| DE | 10222359 B4 | 12/2003 |
| DE | 102004017018 A1 | 10/2005 |
| EP | 0148803 A1 | 7/1985 |
| EP | 0548830 A1 | 6/1993 |
| EP | 1125112 B1 | 8/2001 |
| EP | 1308715 A | 5/2003 |
| EP | 1396739 A1 | 3/2004 |
| EP | 1591825 A | 11/2005 |
| WO | WO 0212863 A | 2/2002 |

* cited by examiner

METHOD AND APPARATUS FOR THE EXAMINATION OF SPECIMENS

BACKGROUND OF THE INVENTION

1. Field of the Invention

The invention relates to a method, in which specimens are examined with a microscope. For the illumination of the specimen, spatially coherent light in at least one continuous or continuously tunable wavelength range is generated. One or more wavelengths or ranges of wavelengths of the illumination light are selected in dependence on the specimen and/or the specified method of examination. The specimen is illuminated with the selected wavelengths or wavelength ranges. The illumination light and the emission light coming from the specimen are separated into separate beam paths. The illumination light is radiated back by the specimen and is suppressed in the beam path before the detection, and the emission light is detected. Further, the invention relates also to microscopes with which a specimen is analyzed—in particular by means of such a method. The present invention is concerned with the problem of the use of light sources, which emit spatially coherent light with a broad wavelength range, in microscopy, especially in fluorescence microscopy with Laser Scanning Technology (LST), and with the problems found in the obtained images, which arise in the use of the invention.

2. Description of Related Art

Use of broadband emission or variable broadband light sources in laser microscopy is attracting increasing interest recently. Its advantage lies in the free selection of the wavelength, which enables flexible adjustment of the different wavelengths that are needed in the excitation of the dyes, with which the specimens to be examined are marked. Use of such sources, which emit broadband, spatially coherent light, is described, for instance in U.S. Pat. No. 6,611,643. In that publication, a microscope apparatus comprising a laser is disclosed, in which the radiation is coupled in the microstructures of a fiber, in which broadband light is generated. However, the details concerning how the microscope itself is to be embodied, enabling it to use the broadband light in a suitable manner for various methods of examination, are not provided in the patent.

Instead of generating broadband light with microstructured fibers, the light can also be generated by exploiting the special properties of doped glass fibers, which are easier to handle than the aforementioned microstructured fibers. Such methods are described, for instance, in the article of Tauser et al in "Optical Letters" vol. 29 on pages 516 to 518.

A broadband laser illuminator is also described in U.S. Pat. No. 6,796,699. Here as well, however—apart from a general reference to the possibility of adaptation of the illuminator—no concrete technical embodiment for the adaptation of such an illuminator is described in the context of microscopy. Similarly, in U.S. Pat. No. 6,888,674 B1, only the coupling with a source with spectral broadening in a laser scanning microscope, abbreviated as LSM in the following, is described in very general terms, whereby the use of acousto-optical filters (AOTF), acousto-optical deflectors (AOD), acousto-optical beam splitters or LCD attenuators is concisely described.

In U.S. Pat. No. 6,654,166, the illumination of an LSM with an illumination unit is described, in which spectral broadening is generated with a microstructured fiber and a special beam splitter. The beam splitter is thereby a central element in the LSM, which must be specially adapted to the issues related to imaging and manipulation. The beam splitter described in U.S. Pat. No. 6,654,166 is embodied as a polarization- and wavelength-dependent element, which can also be prepared with a broadband reflecting coating, for example, of silver or aluminum. One must note, however, that in this embodiment there is the disadvantage that considerable losses result in the detection beam path. In particular, in fluorescence microscopy, these losses can lead to the failure of the method.

In combination with a broadband emitting or a variably tunable broadband laser, an accordingly suitable, flexible main dichroic beam splitter is required, which separates the excitation light from the light to be detected. A flexible main dichroic beam splitter, which operates in the visible range of the spectrum and which is realized using an acousto-optical component, is an acousto-optical beam splitter (AOBS) such as that described in US 2005/046836 A1. For a continuously tunable or broadband excitation from ultraviolet to near-infrared spectral range, this type of AOBS is not suitable. For the mentioned spectral range, at least three different geometries or embodiments are necessary. Besides that, such an AOBS, which is designed for excitation with narrowband laser lines, possesses only a small spectral selection width, and hence has low efficiency particularly in the context of a broadband light source. A flexible adaptation of a continuous spectrum to a method of examination is thus not possible. This disadvantage, namely, that only one or more discrete lines of the spectrum can be selected for the excitation, applies also to the main dichroic beam splitters, which use a polarizing rotation by means of AOTF for the spectral separation.

This disadvantage can be avoided by means of additional components, which enable continuous spectral splitting of the light and at the same time manipulation in this spectrum, definable with respect to the spectral position. Such additional components are proposed, for instance, in DE 19 15 102 and U.S. Pat. No. 6,633,381 B2. The arrangement described there has the disadvantage that three prism spectrometers—one each before and after the dividing element in the excitation beam path, and one in the detection beam path—are necessary. This considerably increases the complexity and the proneness of the arrangement to fail. Further, it is also limited to parallel confocal microscopes with band illumination. Besides that, the variant described in U.S. Pat. No. 6,633,381 B2 has the disadvantage that due to the fixed elements, discrete, predefined wavelength ranges can be separated and detected.

Therefore, the solutions described above do not exploit the full potential of the broadband emitting or variable broadband light sources in the context of their possible applications. The illumination wavelengths, for which, for example, the dyes, with which the specimen is marked, are to be excited to emit, are selectable only to a limited extent. The same applies to the spectral ranges to be detected, in which the solutions available in the prior art are limited solely to the blocks of discrete excitation lines.

In the aforementioned prior art for the coupling of a broadband light source with an LSM as well as for beam separation in an LSM, no further details are provided as to what a flexible method, especially in the context of the imaging, for optimal selection of the illumination and detection wavelengths or bands should look like and no corresponding arrangements are described. One such method is described in US 2005/046836 A1. The illumination and detection wavelengths are thereby selected on the basis of a comparison with a database, based on the characteristics of the dyes with which the specimen is marked. The illumination and the detection spectral ranges are thereby calculated solely on the basis of the individual spectra filed in the databases. As a result, one obtains a setting, which is supposed to be ideal in a purely theoretical sense. However, many object-specific factors, which can have a considerable influence on the results of the measurement, cannot be taken into consideration therein. Included here, for example, is the dependence of the excitation and the emission spectra on the environment of the dye, as has been used in the prior art for some time, as described, for example, in the article of Tsien, Annu. Rev. Neurosci. 12 (1989), page 227 pp. Another example is the appearance of the unknown fluorophores in the object, which can lead—as in the so-called autofluorescence—to undesirable cross excitations.

BRIEF SUMMARY OF THE INVENTION

Therefore, the underlying aim of the invention is to develop a method, as described above, and microscopes, in which the spatially coherent light in at least one continuous or continuously variable wavelength range is generated for the illumination of the specimen, to such an extent that such object-specific factors can be better taken into consideration.

This problem is solved in the context of a method mentioned at the outset, in that the selection of the wavelengths or wavelength ranges of the illumination light with the separation of the detection light and the illumination light as well as the suppression of the illumination light is tuned in such a manner that a prespecified control variable R achieves an extremum. In which case then, optimal imaging is achieved from the viewpoint of the user, that is, tuning is optimized for the imaging.

In the simplest case, for example, the intensity of the light coming from the specimen can be used as the control variable. It depends, in a common epimicroscope for instance, on the absorption, emission and reflection behavior of the specimen. However, these properties depend on their part on the wavelengths with which the specimen is to be radiated.

In a preferred embodiment according to the invention, the specimen is marked with one or more dyes. The dyes are then excited by the illumination light to emit and the emitted light is detected as the emission light. Thereby the above mentioned optimized tuning of the illumination and the detection is especially meaningful, if the wavelengths or the wavelength ranges of the emission light to be detected falls at least partially within the wavelength range of the illumination light, that is, both the emission light and the illumination light lie in an overlapping range in the visible spectrum.

It is of advantage, if the wavelengths or the wavelength ranges of the illumination light are varied for tuning in prespecified steps. In each step, one or more images are detected and thereafter a control variable is determined, in general on the basis of the registered image data. In each step, the separation of the detection light and the illumination light as well as the suppression of the illumination light are also adjusted, so that finally the control variable is obtained as a curve in dependence on the wavelength or, for example, on the mean wavelength of the wavelength range. Various control variables can be foreseen, for example, the mean intensity of the image, the contrast between two selected points in the image, or the signal-noise ratio, whereby these variables are then maximized.

In an advantageous embodiment according to the invention, the detection can also be done with spectral resolution. It is preferable, that the spectral ranges to be detected are also included in the tuning and in each step these values are also varied with respect to the illumination light. Such an optimal tuning of the spectral ranges to be detected is meaningful, especially if the wavelength-dependent cross excitations of different dyes are involved. The optimal tuning of the variables with respect to each other is more effective, if it is done with a reference specimen that is effectively identical with the actual specimen, that is, with a reference specimen, which is marked with the same dyes, and whose chemical environment is the same as that of the actual specimen. Alternatively, the tuning can be done with the specimen itself, insofar as the bleaching effects play a subordinate role, that is, the mean dye concentrations in the image field remain practically the same during the tuning. The tuning can be done for the object segment that is relevant for the later imaging. In the case of probe which remain static during the time necessary for optimal tuning, the images can be used in the context of this optimization for the averaging of the image to improve the signal-noise ratio (SNR).

Such a fast tuning is, among other things, of decisive importance for the starting configuration, that is, for the initial setting of the wavelengths or the wavelength ranges, as well as, if applicable, the detection spectral ranges in connection with the corresponding settings of the components in the microscope. It is advantageous if the wavelengths or the wavelength ranges of the illumination light, which are set at the beginning of the tuning, are selected on the basis of a database. Where applicable, the spectral ranges to be detected are also selected on the basis of the database. In the databases, the excitation and the emission spectra of these dyes are stored, if applicable, in dependence on the solvents.

In an advantageous embodiment according to the invention, the selection of the wavelengths or the wavelength ranges of the illumination light as well as, if applicable, of the spectral ranges of the emission light takes place completely automatically, whereby, as a rule it is meaningful, if the user presets a start configuration. This can be done either on the instrument itself or in the system for regulating the microscope where the system is provided with information about the dye types, so that the system can select an appropriate start configuration from the database. If such databases are not available, it also makes sense if the user manually selects the wavelengths or wavelength ranges of the illumination light and the emission light.

In the simplest case, for instance, if the specimen is marked with only a single dye and the result depends solely on the intensity of the laser light radiated back by the specimen, one preferably uses the sum of the mean intensities over the detected image in dependence on the wavelengths or wavelength ranges of the illumination light as the control variable R. Therefore, with each optimization step for optimal tuning or for tuning of the extremum of the control variable R, at least one image is taken. Alternatively, several starting configurations can also be tested, for which it is necessary, to take more than the image per optimization step. For each image, its mean intensity is calculated and summed.

However, there are cases, in which this simple selection of the control variable fails. This is the case, for instance, if, during the optimization, there is cross excitation with other dyes in dependence on the wavelength. If the emission light is detected with spectral resolution and if the emission spectra of the additionally excited dyes are known, the spectral separation can be accomplished. As a rule, preferably the difference of the mean intensities of two or more spectral ranges in the detected images in dependence on the wavelengths or wavelength ranges of the illumination light from different regions of the image is used as the control variable.

In the preceding example, the spectral separation of the spectra takes place computationally. If only one additional dye is present, determination of the mean intensity is sufficient. The first spectral range is fixed about the maximum of the emission of the dye to be imaged. As the mean intensity, one obtains then, for example, a value $I_s$. As the second spectral range, that range is selected, in which the emission of the additional dye lies, and determines the mean intensity $I_c$ there. If the control variable is denoted by R, one obtains in this case $R=I_s-I_c$. A variation and/or optimization of the spectral range for the emission light must not take place in this case; the range can remain constant. One can also dispense with the detailed spectral resolution completely if a spectral separation of the desired signal and cross excitation signal is possible in at least two channels without problems.

In another embodiment according to the method, the difference between the mean intensities of two selected regions in the images is dependent on the wavelengths and wavelength ranges and is used as the control variable. This is particularly appropriate if a spectral separation as in the aforementioned example is not possible. Then as the first region that region is defined, for instance, as the region containing the desired signal. The second region in the image is defined as the background region. In the latter case, the interfering light, which in the example above is primarily the intensity of the emission due to the cross excitation, is detected, while in the first region, the essential part stems from the detection of the desired intensity. In both cases, it can be, for instance, the intensities of the fluorescence signals. The control variable R is obtained as the difference of the intensities of the first and the second region, $R=I_1-I_2$. For a simpler presentation, the control variable can also be normalized in that it is divided by the sum of the intensities. Preferably, in the calculation of R, the weighted and normalized intensities from the first region in additive form, $w*I_1/I_1^{max}$ are taken into consideration. In this formula, "w" is a selectable weight factor. In this manner, one can additionally take into account the signal-to-noise ratio in the desired intensity in the optimal tuning.

Moreover, the invention relates also to microscopes comprising a laser, which continuously emits light with a wavelength range or which can be tuned to emit light in that range and act as the source of illumination. A first selector device is used for selecting a wavelength, a wavelength range, several wavelengths or several wavelength ranges of the illumination light. Separators separate the beam paths of the illumination light and the emission light that comes from the specimen. A suppressor device provides for obstruction detection of the illumination light that is radiated back from the specimen and reaches into the detection beam path, as well as the detection device for the detection of the emission light. In this way, the illumination source, the first selector, the separator and the suppressor can be regulated and can be variably adjusted in regard to the wavelength selective properties. In such a microscope, the aforementioned task is solved in that a control unit for the regulation and mutual tuning of the first selector, the separators and the suppressor on the basis of the control variable R are provided, so that this control variable takes an extremum. Preferably it involves a Laser scanning microscope, because in that case, the microscope with such an embodiment can be optimally adapted by means of a control unit to the various methods and conditions of the examination.

Preferably, input devices for the input or the selection of the examination method and/or specimen properties are provided in such a microscope. Inputs can include, for example, the dyes, with which the specimen is marked, or special methods for the excitation of fluorescence, such as a single-photon or a multiphoton method. In the latter case, additional adjustment of the illumination light in connection with the optimization can be of advantage, in order, for example, to influence the pulse variables of the laser, such as, for example, the pulse duration and pulse repetition rate.

The control unit is preferably designed for automatic tuning of the first selector, the separator and the suppressor devices. After the entry of the initial configuration, for example, the control unit is automatically set to a start wavelength range, matching accordingly the transmissibility of the separator. The suppressor devices are regulated. In the next step, this is repeated for another wavelength or another wavelength range. After that, computation on the basis of the comparison of the control variable for each configuration, as well as the subsequent determination of the extremum as well as the optimum of the control variable takes place in the control unit. The configuration is then adjusted according to this optimum.

In another advantageous embodiment of the microscope, devices for spectral resolution of the emission light are provided. This enables, for example, resolution of the light coming from a specimen marked with several dyes separately. Thereby it is of advantage to provide a second selector for the selection of one or more wavelength ranges, in which the emission light is detected. Especially in the case when the wavelength ranges of the illumination light overlap the ranges of the emission light, such a selection is necessary.

Preferably, the control element is designed also for the regulation and tuning of the second selector with the first selector, separator and suppressor on the basis of the control variable. Even a combination of the second selector with the suppressor or integration with it is possible. In this manner, the wavelength ranges can be mutually tuned optimally for the excitation light as well as for the emission light in regard to their positions, their widths and their intensities.

Preferably, in the first selector, one or more acousto-optical filters, in particular acousto-optically tunable filters (AOTF) or acousto-optically tunable modulators (AOM) are provided. The advantage of AOTF compared to the AOM technology lies above in that, more than one wavelength or a spectral range can be selected at the same time from a broad spectrum by separating the first order diffraction. This is therefore an important property, because the dyes allow excitation with a dye-dependent spectral width and hence the available laser power of the broadband laser source can be better exploited. Therefore, in connection with the aforementioned optimal tuning of the excitation, as greater flexibility with respect to the spectral width as possible is of great advantage. AOTF's according to the prior art have a very low spectral width or a high spectral sharpness in the region from 0.5 to 2 nm. Conceivable also are technical embodiments of such AOTF's, which realize greater spectral widths with otherwise identical properties, for example, a width of 25 to 30 nm for a mean wavelength of 490 nm, and a width of 60 to 65 nm for mean wavelength of 670 nm. The width of the spectral window of an AOTF is as a rule an invariable property of the system.

An AOM according to the prior art realizes a greater spectral width for the correspondingly set acousto-optical frequency than an AOTF. The spectral width lies, for example, in the near-infrared range at about 20 nm and in the range of 490 nm to 640 nm at about 20 to 40 nm. AOMs can be tuned in the visible range above about 150 nm, thus this range is somewhat smaller than in the case of an AOTF, which can be tuned above 250 mm.

Therefore, in order to be able to select a larger spectral range or several smaller spectral ranges, the filters, that is, AOM and/or AOTF are connected in series, whereby each AOM and/or AOTF decouples a different wavelength or wavelength range. In which case, it is of advantage, if the devices for the combination of the decoupled wavelengths or wavelength ranges are provided. For example, dichroic beam splitters can be used for that, which are preferably designed as longpass, shortpass or bandpass. If the source of illumination is a laser, which emits very short pulses and it is to be used at the object level for non-linear specimen interactions, then, due to the long continuous glass path in the individual elements—as materials $TeO_2$ or $SiO_2$ come in question here—a dispersion compensation, as it can be realized with grating and prism paths according to the prior art, is necessary.

In a preferred embodiment of the invention, one or more variably adjustable liquid crystal filters are provided in the first selector. With such tunable liquid crystal filters, the illumination light can be spectrally selected on the basis of electrooptical function mechanisms. Among such liquid crystal filters are, for example, the so-called Liquid Crystal Tunable Filter (LCTF). LCTFs are embodied in different forms with spectral ranges from 400 to 720 nm, 650 to 1100 nm, 850 to 1800 nm and 1200 to 2450 nm. The half-life periods of the respective windows, in which the radiation is transmitted, is a constant of the system, as is the case with the AOTF and AOM, and lies, in the case of the first abovementioned spectral range, in the range of 10 nm for the lower wavelength of 400 nm and at about 45 nm for the upper threshold wavelength of about 700 nm. A switching frequency of about 50 Hz enables change of the bandpass range, whereby only one range is possible at any time.

Further, additional components on the basis of the gratings, prisms or monochromators are possible. In another embodiment of the microscope, one or more variably adjustable bandpass filters are provided in the first selector. Such a tunable bandpass filter can be conceived on the basis of the interference filters, with the corresponding fine graduations, in the form of longpass and shortpass filters, as described, for example, in DE 198 35 070 A1 incorporated by reference herein. With it, it is possible not only to cover a larger wavelength range, but also to keep the width of the respective bandpass variable. The smallest graduation in single longpass or the shortpass filters of 10 nm corresponds to the state of the art. The half-life periods of the resulting bandpass are accordingly also of this order of magnitude. A fixed coupling of the FWHM to the wavelength, as in the electrooptical or acoustooptical filter elements described above, does not exist, so that a targeted influencing of the spectral width is possible. Such a bandpass filter can obviously also be used in combination with other components described above. In which case, it is of advantage, if the intensity is also to be modulated, because that is not possible with a bandpass filter.

Other devices for intensity modulation are, besides neutral gray filters, either arranged with discrete graduations on a rotatable wheel or continuous like graduated filters—also the polarization attenuators on the basis of achromatic delay plates in the form of $\lambda/2$—plates in combination with linear polarization filters or polarization beam splitters. Achromatic delay plates can cover spectral ranges of approximately 250 nm in the visible spectrum range and approximately 500 nm in the near infrared range. There are also other possibilities with the use of simple liquid crystal filters. It is suitable if such units are switched in before and after the spectral selection. Other possibilities for intensity modulation exist in the use of components on the basis of polarizing rotation through magneto-optical effects, such as, for example, in the case of Faraday rotators, or through electro-optical effects, such as, for example, in the so-called Pockels cells. Obviously a direct modulation of the laser source, if that is possible in the device, is also possible.

In order to separate the illumination light, with which the dye is excited, from the emission light, the so-called main dichroic beam splitters (HFT) are used especially in fluorescence microscopy with laser beam microscopes. Such a main dichroic beam splitter has, depending on the function, three so-called entry and exit ports. At the first port is the light of the laser source into the main dichroic beam splitter. The exit takes place at the second port in the HFT and is guided to the specimen. At the same time, the second port also serves as the entry port for the light coming from the specimen, among other things also for the fluorescence light generated due to interaction with the specimen. It is spectrally separated from the HFT and guided through the third port to the detector.

It is preferable if a flexible main dichroic beam splitter is provided in the separators, in which the illumination light and the emission light are spectrally resolved and are modified and deflected in dependence on the wavelength. With the modification in dependence on the wavelength, it is possible to separate the excitation light and the emission light efficiently and to guide it to the correct port. In this way, the optical path can be influenced by the mechanical elements in dependence on the wavelength, as described, for example, in U.S. Pat. No. 5,751,417, U.S. Pat. No. 6,633,381 B2 and U.S. Pat. No. 6,377,344 B2 (incorporated by reference herein). Another alternative is to influence the polarization of the light by means of a so-called Spatial Light Modulators (SLM), based, for instance, on liquid crystals.

In another embodiment, an achromatic main dichroic beam splitter is provided in the separators, in which the illumination light and the emission light are imaged in spatially different regions and deflected. In contrast to the previously described flexible main dichroic beam splitters, the spectral bands cannot be flexibly adjusted. Instead, the separation of the excitation and the detection takes place over a broadband. In fluorescence microscopy with a laser scanning microscope, this separation is based on the different spatial coherence of the excitation light and the fluorescence. Since the excitation light is spatially coherent, it can be formed into definite structures through the aperture diaphragm. The spatially incoherent fluorescence light on the side fills the entire aperture diaphragm. If the excitation light is formed similarly and if one makes use of the appropriate reflecting or transmitting structures in the HFT, the excitation light can be directed to the specimen fully and the fluorescence light can be directed to the detector with minor losses.

If a complete separation of the illumination light and the emission light by means of the above described elements is not possible, because, for instance, the wavelength of the illumination light falls in one of the spectral ranges to be detected, it is provided with a device for suppression, which obstructs that such a light reaches the detected. It is preferable if a spectrally selective diaphragm is provided in the suppressor device, which can advantageously be adjusted variably. Such a diaphragm is described, for example, in US 2005/045812 A1.

The method and the microscope described above can be employed preferably in fluorescence spectroscopy or fluorescence correlation spectroscopy, in FRET and FLIM analyses, in the study of multiphoton excitations, in the identification of dyes as well as in the manipulation of probes in general. This illustrative account is obviously not exhaustive, and other applications, especially biomedical and other applications familiar to specialists skilled in the art, are indeed thinkable.

BRIEF DESCRIPTION OF THE DRAWINGS

The invention is explained further in the following on the basis of exemplary embodiments. Shown in the corresponding drawings are.

DETAILED DESCRIPTION OF THE INVENTION

Figure 1:
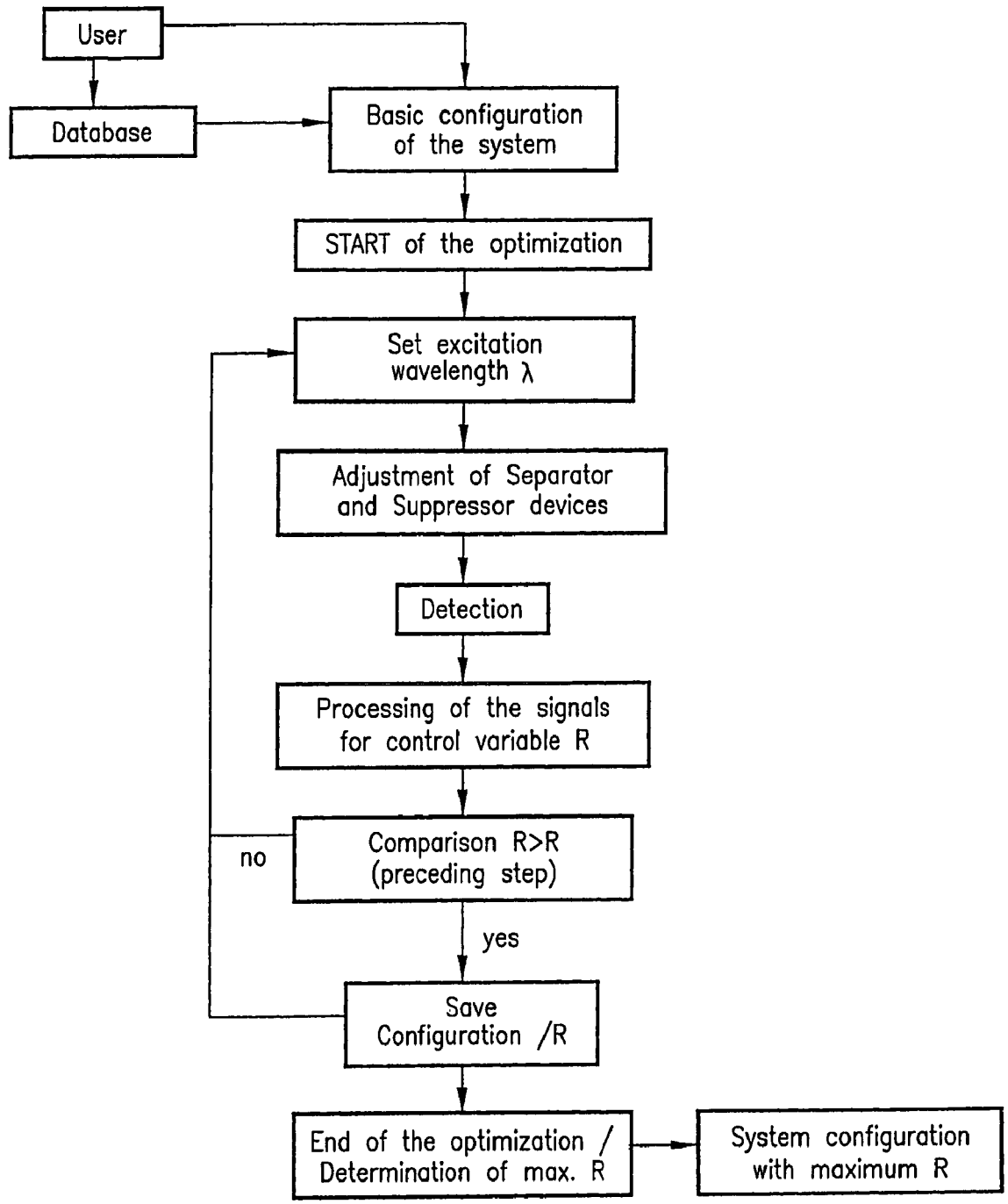
FIG. 1 is a flow chart showing the procedure in the method with a fixed detection wavelength range.

In describing preferred embodiments of the present invention illustrated in the drawings, specific terminology is employed for the sake of clarity. However, the invention is not intended to be limited to the specific terminology so selected, and it is to be understood that each specific element includes all technical equivalents that operate in a similar manner to accomplish a similar purpose.

FIG. 1 shows the procedural sequence of the method for the optimization of the excitation wavelengths for a fixed detection wavelength range. The user can do the basic configuration of the system for the start of the optimization himself or use the emission and detection spectra stored in the database by entering the dyes present in the specimen. In the latter case, the basic configuration of the system takes place automatically on the basis of the information in the database. The other optimization variables, such as the step lengths, excitation and detection bands are set up automatically by the system. Control and processing of these settings is possible by the user before the start of the optimization, however, it is not absolutely necessary. In the example for a fluorescence microscopic measurement presented here, in the context of the optimization—which is done either using a reference specimen or the specimen to be examined itself—the excitation wavelength λ is varied in accordance with a prespecified step length. Alternatively, the wavelength range can be varied. Variation of several wavelength ranges is also possible. Corresponding to the set wavelength, the separator and the suppressor devices are then adapted accordingly and the detection of the light radiated back by the specimen takes place. Advantageously, the plot of the complete image or a stack of images is then shown in the z direction. The detection can however take place only at a single point in the specimen. In each case, the detected signals for the control variable R are processed. For example, R can be defined as the sum of the mean intensities over all displayed images. For the control variable R determined in this manner, comparison is then done, about whether the value determined in this step is greater than the value of the control variable in the preceding steps. If this is not the case, the setting of the configuration for the next excitation wavelength is done and the control variable R is determined again. If the control variable R is maximal in comparison to the values of the control variable R determined hitherto, the settings of the configuration are saved and only after that the setting are adjusted for next wavelength. At the end of this variation of the excitation wavelength, the system is configured according to the maximum value of the control variable R and the saved settings.

Figure 2A:
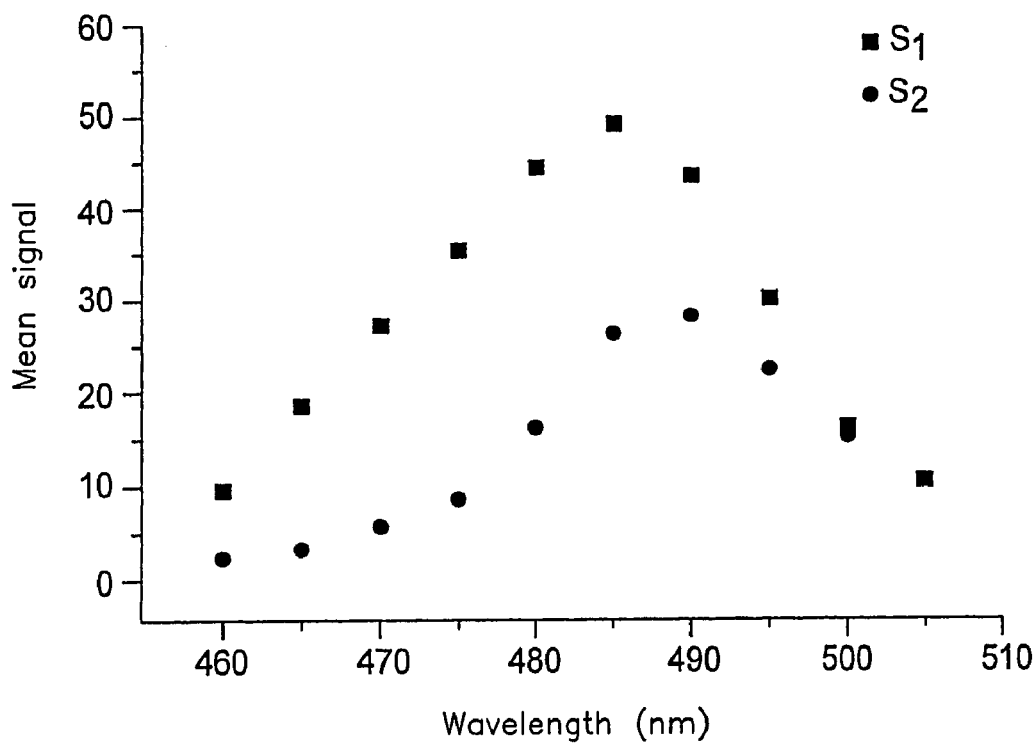
FIG. 2a is a wave diagram showing the signal intensities of two signals from different areas of the specimen.
Figure 2B:
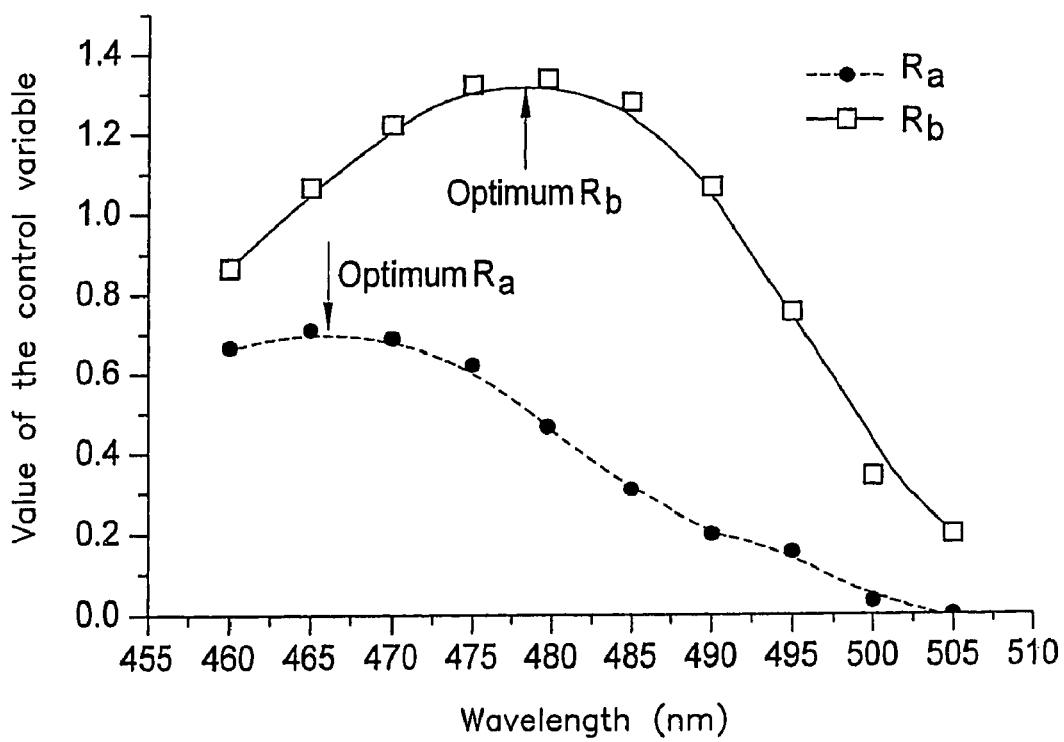
FIG. 2b is a wave diagram showing the curves of two possible control variables.

In FIGS. 2a and 2b, the determination of the control variable for the optimization of the excitation for the case, in which the wavelength dependent cross excitation of several dyes occurs, is shown. A direct separation of the signals or the intensities is not possible in such a case. For this reason, a first region in the image is defined, from which practically the desired fluorescence is detected, and a second region of the image is defined as the background region, from which fluorescence emitted predominantly due to the cross excitation is detected. The average signals or the intensities from the two regions in dependence on the wavelength are shown in FIG. 2a. The step size was 5 nm in this case.

In this case, as the possible control variable, comes, for instance, the contrast of the signal $S_1$ from the first region of the image compared to the mean signal $S_2$ from the background region, $$R_a = \frac{S_1 - S_2}{S_1 + S_2}$$

in question. This control variable is shown in FIG. 2b.

In order to take the signal-to-noise ratio into consideration, the contrast can be enhanced with addition use of the weighted, normalized signal value of the first image region, $$R_b = R_a + w \frac{S_1}{S_1^{max}}.$$

In FIG. 2b, the control $R_b$ for the weight w=1 is shown. As the optimum, one can use, as a first approximation, the value of the control variable for a setting for an actual wavelength λ, advantageously, however, with interpolation from the measured values. In the present case one obtains the respective interpolated, optimal excitation wavelengths, which lie close to the actually set values.

Figure 3:
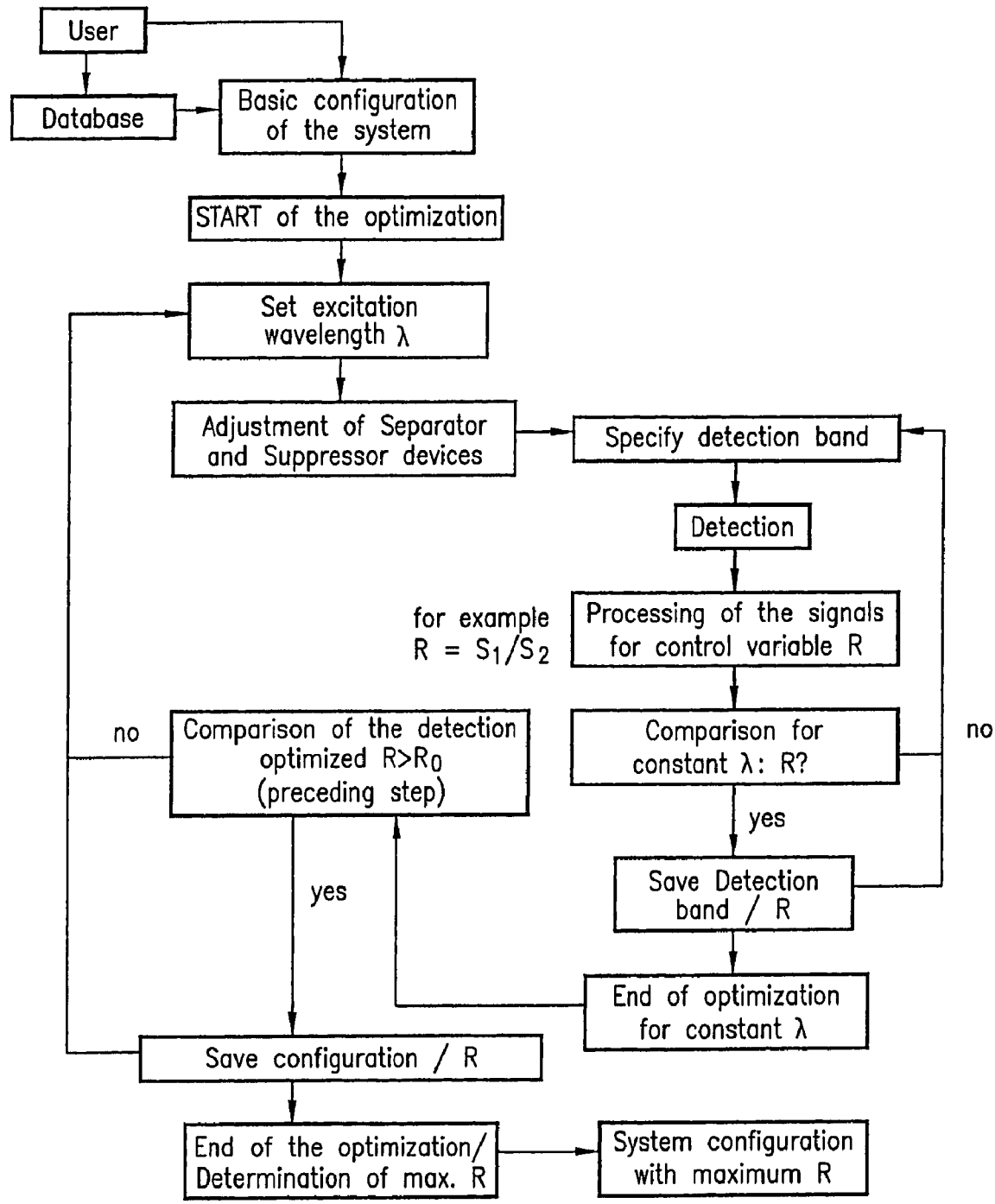
FIG. 3 is a flow chart showing the sequence of the method with a variable detection wavelength range.

In FIG. 3, an enhanced sequence of the procedure compared to the method in FIG. 1 is shown, in this case however for each wavelength step, the position of the detection band or the detection wavelength is also optimized. This can be done, for example, through the adjustment of the separator in connection with the introduction of the various emission filters. Thus, for each excitation wavelength, one obtains a value of the control variable $R_d$ optimized for the detection. At the end of the optimization—as also shown in the procedure in FIG. 1—the maximum of the control variable R is determined, for instance, through interpolation, and the system is accordingly configured.

Figure 4:
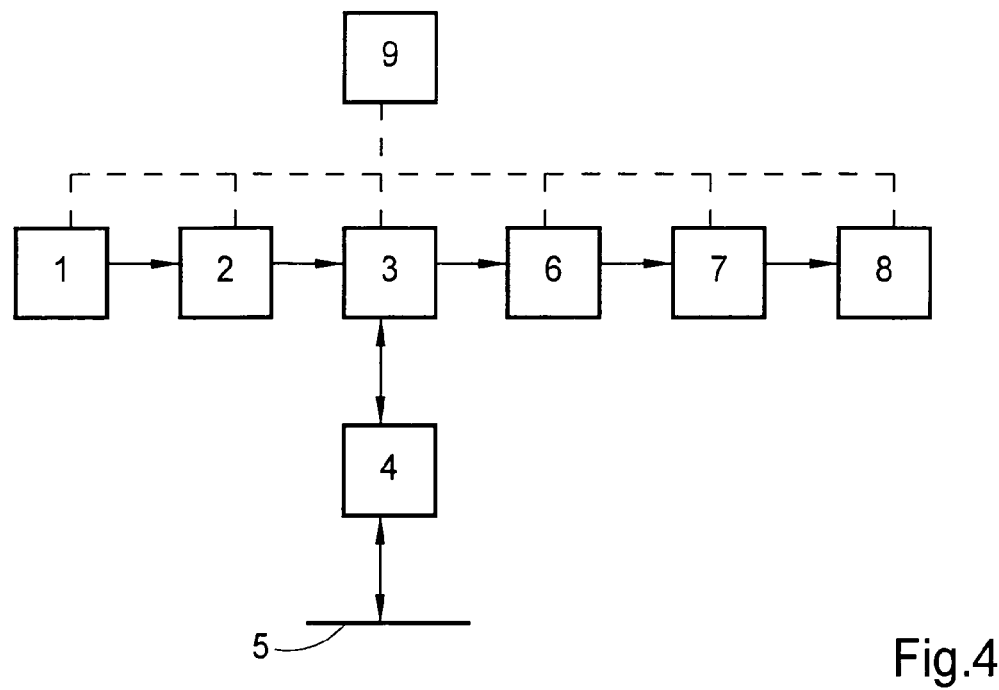
FIG. 4 is a block diagram explaining the principle of a microscope used with the invention.

In FIG. 4, a sketch of the principle of the microscope according to the invention is shown. On the left side, there is an illumination source 1, which comprises a laser continuously emitting light with a wavelength range, or is tunable in that range. From the source of illumination 1, the light is emitted and deflected onto the first selector 2. In it, the selection of a wavelength or a wavelength range, several wavelengths or wavelength ranges of the illumination light takes place. The wavelengths or the wavelength ranges selected for further transmission are deflected to separator 3. The latter serves the purpose of the separation of the beam paths of the illumination light and the detection light coming from the specimen 5. The arrows indicate the directions of the beams. Light with the selected wavelength ranges is deflected through the image module 4 onto the specimen 5. If the specimen 5 is marked with fluorescence dyes, the illumination light is absorbed. The excited dyes emit light with other wavelengths that are radiated back to the separator device 3. By means of the separator 3, the emission light, which includes, besides the emission wavelengths, also a part of the illumination light, reflected, for instance, by the specimen, is directed to the suppressor 6, where this part of the illumination light is eliminated. The emission light is then deflected to the second selector 7, in which one or more wavelength ranges are selected in which the emission light is to be detected. The suppressor 6 and the second selector 7 can be embodied also as a single component.

From the second selector 7, the light finally reaches the detection device 8, which can include, for instance, a photomultiplier (PMT) or a CCD camera. The image generated by the computer from the detected values is saved. Further, the microscope according to the invention also includes a control unit 9, which is connected with the illuminators 1, the first selector 2, the separators 3, the suppressors 6, the second selectors 7 as well as the detection devices 8. By means of the control unit 9, the individual components are regulated and, as described above, are optimally tuned to each other. The algorithm can thereby be processed by the hardware circuits or by a suitable program, or a combination of both. Manually tuned control is also possible.

Figure 5:
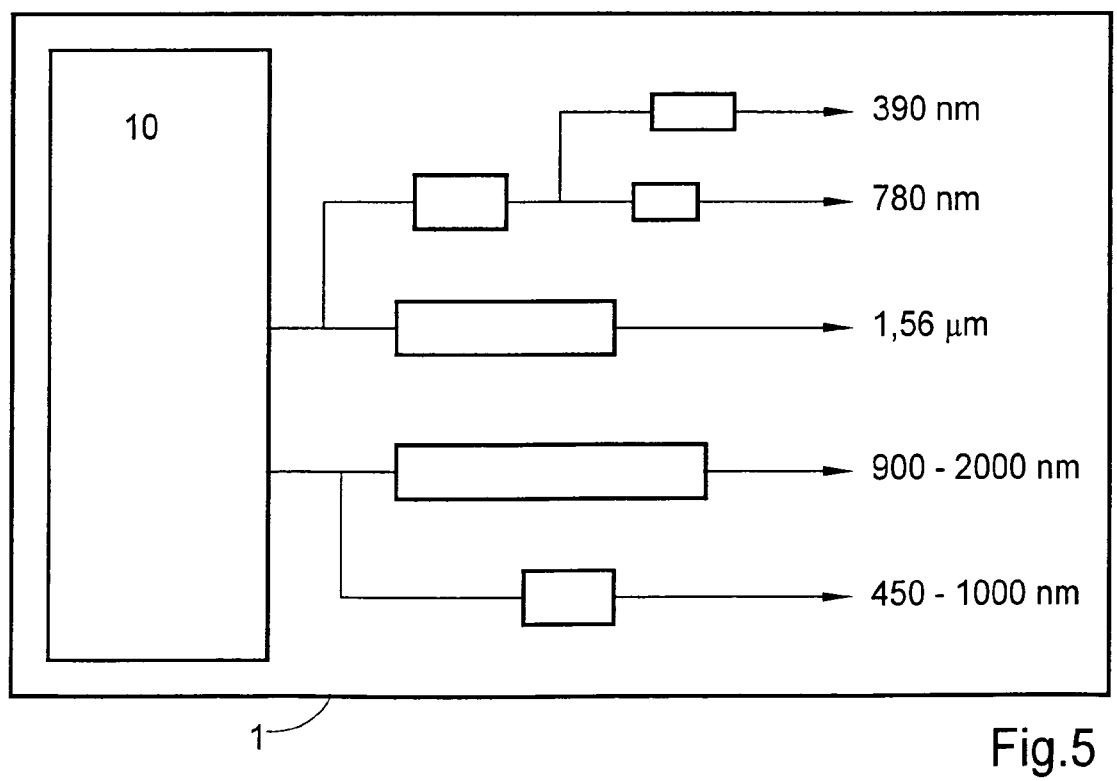
FIG. 5 is a block diagram showing an illumination source for generation of illumination light with several wavelengths or wavelength ranges.

In FIG. 5, an illumination source 1 is shown by way of example, with which light with different wavelengths as well as different wavelength ranges can be generated. The basis of the system is an erbium fiber laser 10, which emits pulsed laser radiation with 1.56 μm and with spectral width of the pulse of about 50 nm as well as pulse length in the range of 100 fs or less through the direct emission of the amplifier system. The frequency of this radiation can be converted, for example, through continuum generation in a dispersion-shifted, doped glass fiber or in a nonlinear crystal—or also in combination. This method is described by F. Tauser et al. in Opt. Let. Vol. 29, No. 5, of Mar. 1, 2004. From the radiation of the erbium fiber laser 10, direct light with wavelengths 780 nm and 390 nm can be generated using the nonlinear methods of frequency doubling. With the generation of a nonlinear continuum, radiation with pulse length of about 100 fs can be generated additionally, which can be tuned in the range from 900 nm to 2000 nm. This on its part enables—also through the nonlinear methods of frequency doubling—a shift of the tuning range into the visible range. Thus, in principle, additionally the spectral range from 450 nm to 1000 nm can be covered with it.

In the spectral range from 450 nm to 900 nm, the spectral width of the laser pulse lies between about 10 nm in the shortwave range and 45 nm partially in the longwave range. In this manner one obtains a single source of light, which can deliver laser light in the range from 390 nm or 225 nm to 2000 nm. The different wavelength ranges can be made available simultaneously, with the facility of simultaneous tunability within these ranges. By means of the first selection device 2, a wavelength range or several wavelength ranges can also be divided externally. In the application, this has the advantage that in the experiments, which are configured for several laser lines that are simultaneously available, no time-intensive tuning of the laser is necessary for the imaging, as is the case, for instance, with titanium-sapphire systems.

In the use of LSM in the context of biomedical applications, which are highlighted here as an important example, the essential contrast mechanism is fluorescence. Fluorescence dyes have specific excitation mechanisms, in which the laser beam to be used for the excitation must be tuned. Thereby, a fluorescence signal can be generated, that is, photons of the laser light source are absorbed by the specimen 5, if the laser emission and the excitation spectrum of the dye present in the specimen 5 overlap fully or in part. In most cases, the emission spectrum of the fluorescence dye is displaced, compared to the excitation spectrum, toward the longwave spectral range as a result of the energy losses due to absorption. This so-called Stokes shift between the two spectra is, however, often so slight, that a complete separation of the spectra in the detection cannot be achieved with simple devices and it often leads to partial overlap of the excitation and the emission spectra. Therefore, in the visible range of the spectrum, an exact selection of the laser light reaching the specimen is necessary, in order to not produce unnecessary stray light that can be removed on the detection side only with difficulty.

Figure 6:
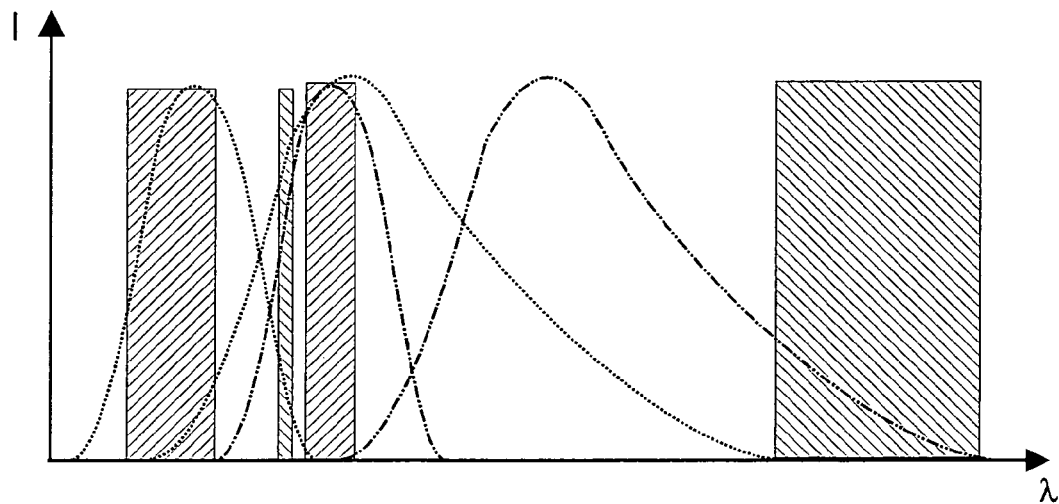
FIG. 6 is a wave diagram showing an optimized setting of the wavelength ranges for illumination and emission light for a specimen marked with two dyes.

In FIG. 6, the conditions in the case of double-dyes and overlapping excitation and emission spectra of the involved dyes are shown. The spectra of the first dye are shown with dotted lines, the spectra of the second dye are shown with dash-dot lines. In both cases, the excitation spectra and the emission spectra overlap, so that unambiguous analysis of the experiment is possible only with exact knowledge of the respective spectra and the simultaneous tuning of the excitation and the detection. Therefore, a broadband emitting or broadband tunable light source can be used meaningfully only if it is possible to detect, despite the broadband nature of the excitation and the presence of the stray light. In FIG. 6, the wavelength ranges for an optimized excitation or detection for both the dyes are represented by rectangles with different shading. Thus, in the experiments, a major part of the laser light used for the excitation must be suppressed as completely as possible. In connection with the just described illumination source 1, other additional components are necessary.

One part is realized with the first selector device 2, in which, in particular, the use of the acousto-optical filters appears obvious. To that count the aforementioned AOTF and AOM. The width of the spectral window of an AOTF is, depending on the wavelength range, about 30% to 50% greater than the spectral width of the laser light, so that, in this case, it is always possible to use almost the entire energy of the laser. In connection with a broadband emitting laser, an AOTF is suitable above all for the spectral selection in view of the fact that with AOTF, spectral ranges outside the selected windows are effectively suppressed. It acts additionally as a fast switch with threshold frequency of about 500 Hz and is in a position to modulate or set the energy of the laser beam quasi continuously.

Figure 7:
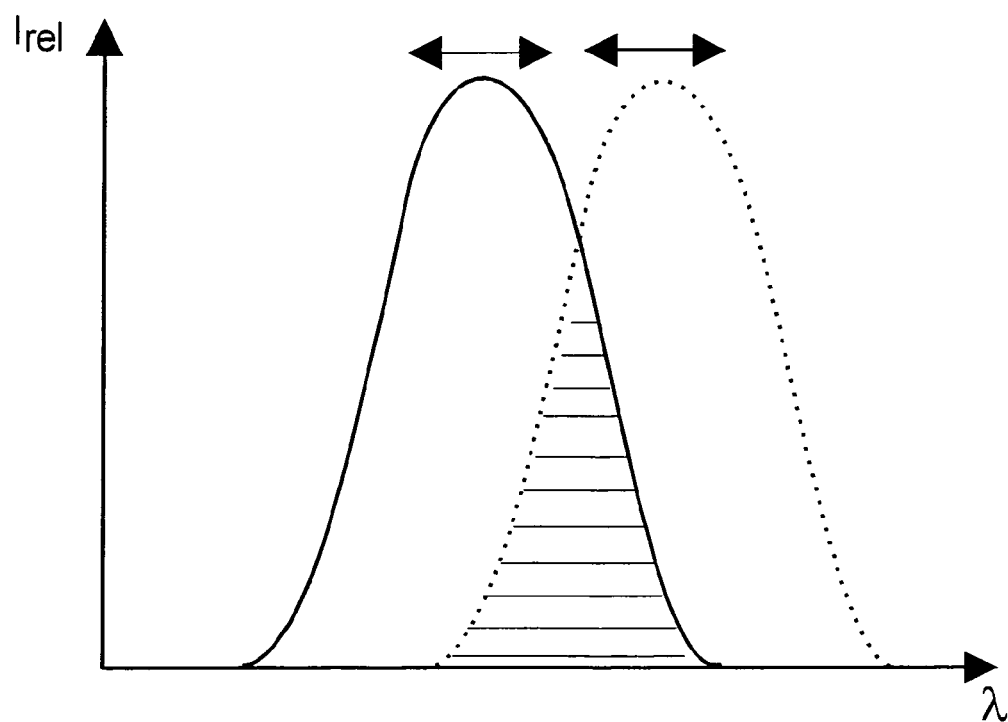
FIG. 7 is a wave diagram showing the wavelength selection with the tuning of the illumination light spectrum and the spectral bandpass range of an AOTF.

FIG. 7 illustrates how one can vary the width of the spectral window. One shifts, in the case of lasers with broadband tuning, the center frequencies of the laser and the broadband AOTF towards each other. In FIG. 7, the spectrum of the laser is denoted by a continuous line indicating a uniform intensity distribution in dependence on the wavelength; the bandpass range of the AOTF is shown with a dotted line. Both the arrows at the maxima of the spectra, which coincide at the center frequencies, indicate the displaceability of the spectra toward each other. Now, if both the center frequencies are shifted towards each other, only a part of the spectrum is transmitted through in the shaded overlapping region of the two spectral distributions and used. Another alternative lies in combination with an additional element, such as, for example, a variable bandpass on the basis of an interference filter with fine graduation. In addition, it is also contemplated that the broadband and the narrowband AOTF's are integrated in a component, so that the width of the selected spectral ranges is selectable by choosing the corresponding AOTF in the context of the acousto-optical technology while taking the spectral intensity of the source into consideration.

The AOM have, on the other hand, spectral width for the set acousto-optical frequency compared to an AOTF; it lies at about 20 nm in the near-infrared range, and between 20 and 40 nm in the visible range. Its tunable range is about 400 to 500 nm in the near infrared, with a maximum of 150 nm in the visible spectrum. The tunable range, with the value of about 250 nm in the visible spectral range, is thus slightly smaller than that with the AOTF. Therefore, in order to carry out the spectral selection and intensity modulation with an AOM, in a spectral range of 450 to 700 nm for instance, a layout in series with several AOM's is advantageous.

Figure 8:
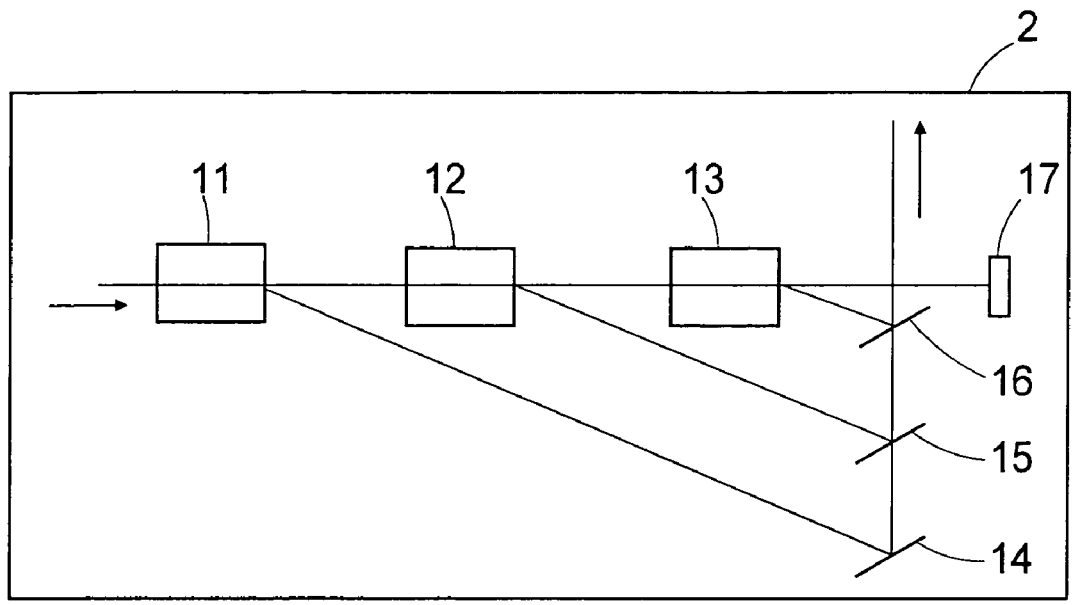
FIG. 8 is a schematic diagram of a layout in series with several AOMs.

In FIG. 8, such a layout in series, with three AOM's 11, 12, 13, is shown. Therein, they are so set up that following the passage of the AOM's 11, 12, 13 in the direction of the beam—in the figure from left to right—the longwave parts of the spectrum are increasingly selected and the undiffracted zeroth diffraction order of the preceding AOM's 11 and 12 enters into the subsequent AOM's 12 and 13, respectively. The orders diffracted away from the optical axis by the AOM's 11, 12, 13 are combined by means of a mirror 14 and the dichroic beam splitters 15, 16 and coupled again parallel into the beam path. Against that the undiffracted orders are swallowed by the beam trap 17. In the example shown, the AOM 11 could deflect the range from 450 to 490 nm, whereas the AOM 12 could deflect the wavelength range from 490 to 640 nm and the AOM 13 could deflect the wavelength range from 640 to 700 nm.

With the help of a separator 3, the excitation radiation is separated from the emission radiation. In LSM, so-called main dichroic beam splitters (HFT) are used in general. Such an HFT separates the excitation spectrum and the detection spectrum and comprises three so-called entry and exit ports, depending on the function. Through the first port $P_1$ the light is efficiently guided to the specimen. Through the second port $P_2$, the fluorescence light generated due to the interaction of the illumination light with the specimen is spectrally separated from the laser light. Finally through the third port, the fluorescence light is guided efficiently to the detector.

Figure 9A:
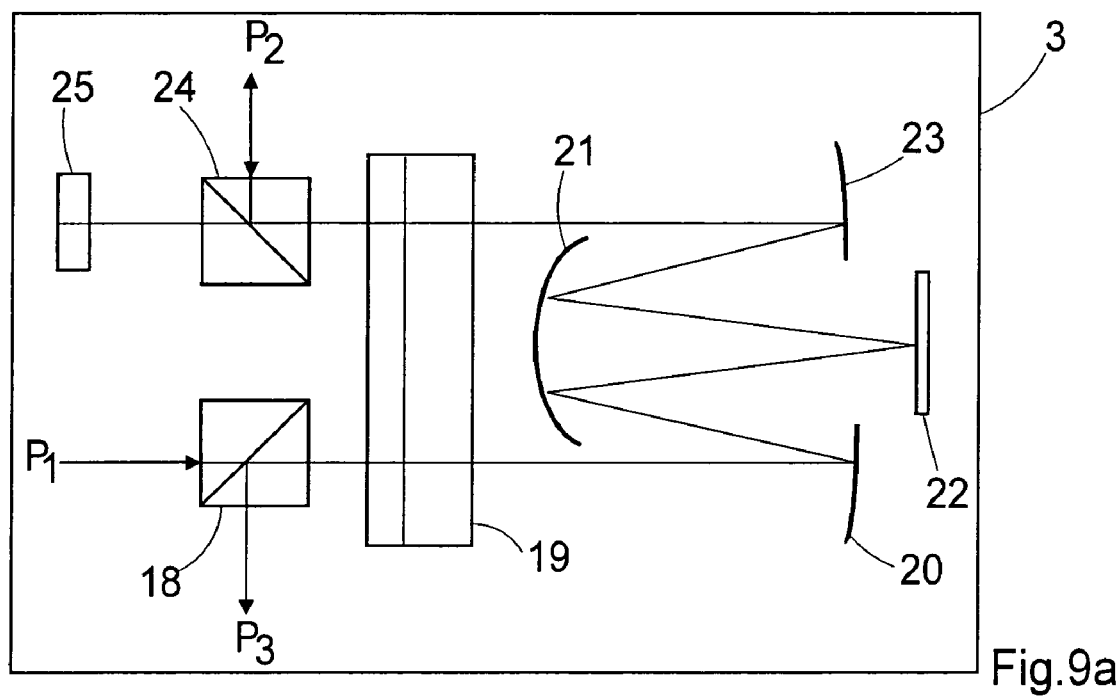
FIG. 9a is a schematic diagram in top view of a variable main dichroic beam splitter with geometric beam splitting.
Figure 9B:
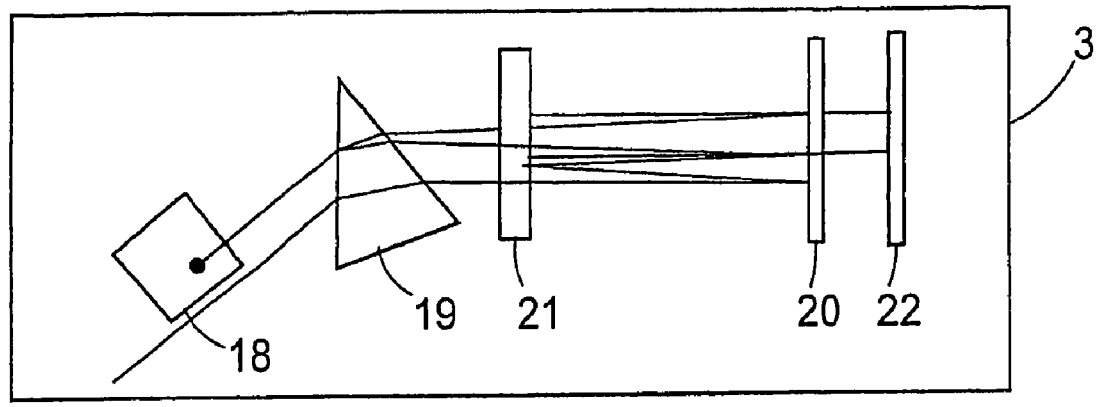
FIG. 9b is a schematic diagram of a side view of the variable main dichroic beam splitter.
Figure 10A:
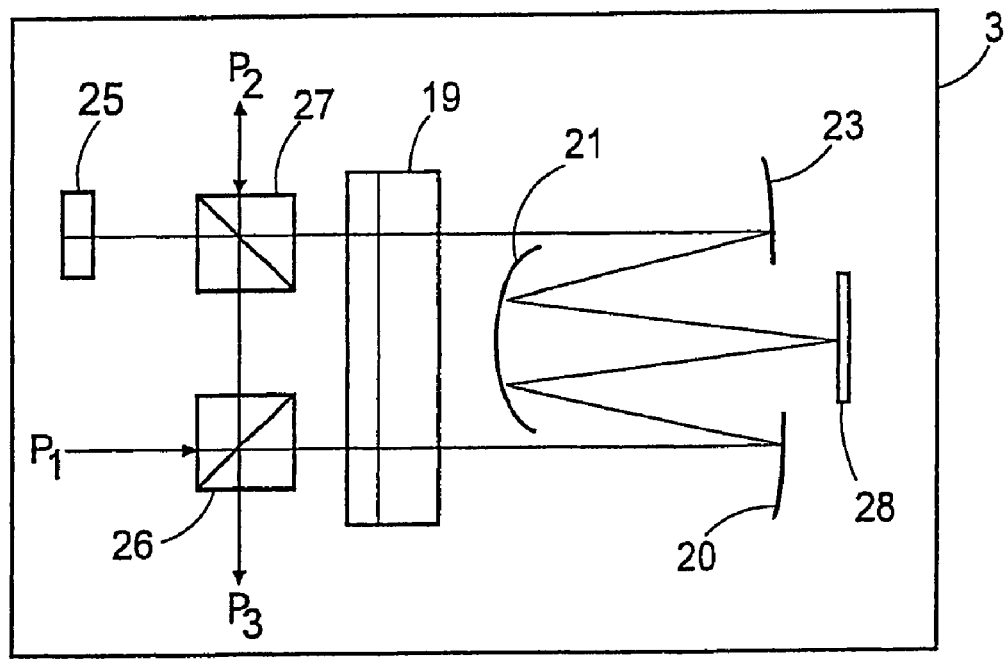
FIG. 10a is a schematic diagram of a top view of a variable main dichroic beam splitter.
Figure 10B:
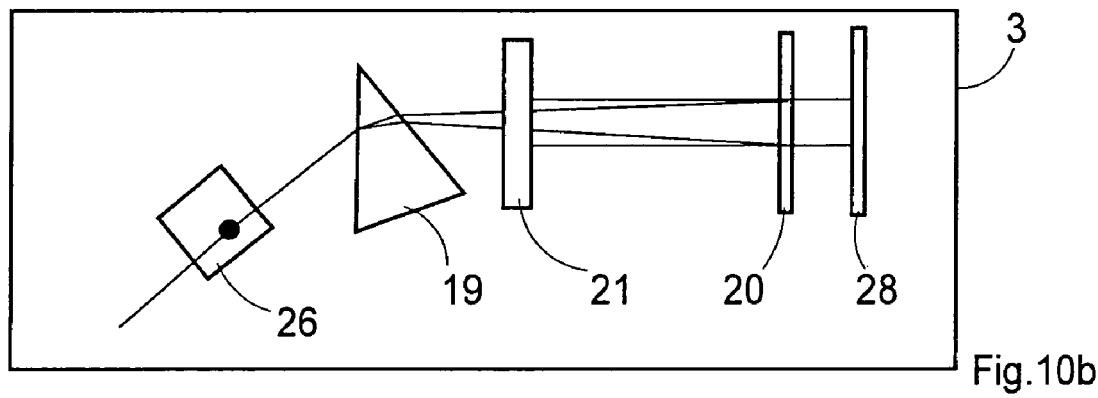
FIG. 10b is a schematic diagram of a side view of the variable main dichroic beam splitter.

In FIGS. 9*a* and 10*a*, these ports $P_1$, $P_2$ and $P_3$ are indicated accordingly. Both of the figures show the top views of the possible embodiments of such an HFT. The corresponding side views are shown in FIGS. 9*b* and 10*b*, respectively. In both cases, emphasis is on the so-called variable main dichroic beam splitters, which are flexible in the selection of the spectral bands for the excitation and the detection. The excitation light and the fluorescence light emitted from the specimen is spectrally dispersed and then modified in regard to its properties in dependence on the wavelengths in such a manner that it leaves the HFT through the provided port $P_2$ or $P_3$. In the variant of the variable HFT shown in FIGS. 9*a* and 9*b*, the excitation light and the emission light are separated geometrically. The illumination light falls at first on a beam splitter 18 and passes unobstructed through it. The light is spectrally dispersed by the prism 19. By means of the mirrors 20 and 21, the light is deflected onto a switching element 22, which can be a mirror array with mirrors that can be individually regulated. The beam coming from the source of light is deflected, according to the wavelength by the mirrors, through the deflecting mirror 23, the prism 19 and another beam splitter 24, onto either the specimen or a beam trap 25.

Instead of influencing the optical path by means of switching of the mechanical elements, the HFT can also be built on a polarization optical basis. Such an arrangement is shown in FIGS. 10*a* and 10*b*. Instead of the simple beam splitter as in the preceding example, polarizing beam splitters 26 and 27 are used. The switching element 28 serves here not for the purpose of directional deflection, but of polarizing rotation, and can be embodied, for instance, as a liquid crystal, which functions as a wavelength dependent delay plate.

By means of the suppressor 6, the laser light used for the excitation is hindered from reaching the detector. Thereby the so-called emission filters are used, whose design or the geometry differ according to the subsequent detector in the path.

Figure 11:
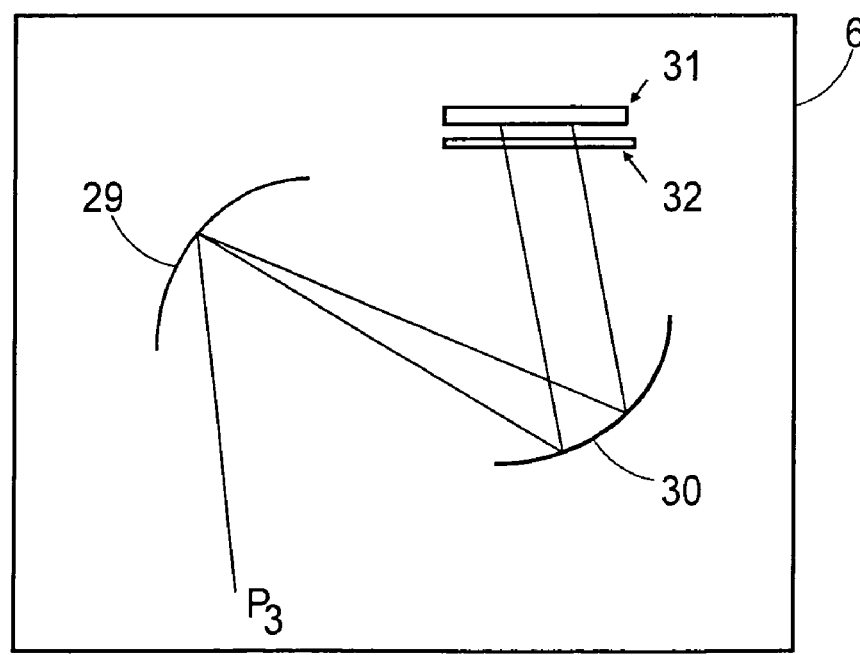
FIG. 11 is a schematic view of a suppressor device for spectral selection and suppression of illumination light before the detection.

A possible arrangement includes use of a spectrally selective diaphragm, with which the light used for the excitation is blocked in targeted manner, as indicated in FIG. 11. The light coming from the main dichroic beam splitter is at first spectrally dispersed using a grating 29 and is deflected through a mirror 30 onto a diaphragm array 32 arranged before a line detector 31. The individual diaphragms of the diaphragm array 32 can be embodied, for instance, as beam traps and are preferably electronically controllable, so that they can selectively open or block the beam path to the line detector 31. This opens additionally the possibility of the simultaneous detection of several spectral bands.

Figure 12:
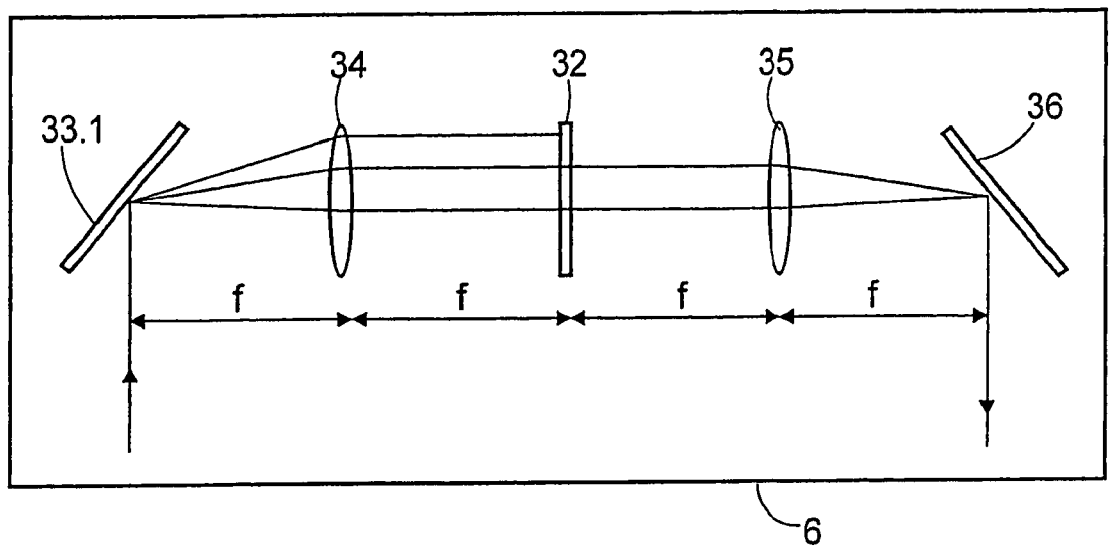
FIG. 12 is a schematic view of a second variant for the spectral selection.

In the case of detection with a single detector also, spectrally selective blocking with a diaphragm array can be achieved. If no large-area, integrating detector is used, the spectrally dispersed radiation must be combined again before the detection. This can be achieved by employing at least one more dispersion element in combination with, for example, a 4-f arrangement. An example of this type of arrangement is shown in FIG. 12. The light coming from the HFT falls at first on the grating 33.1, in which it is spectrally dispersed and imaged onto a lens 34. The individual parallel beams fall on the diaphragm array 32, where they are either transmitted or blocked, depending on the wavelength. In the example shown, the upper beam is blocked, while both the other beams can pass through. From the lens 35, whose focal length is f like that of the lens 34, the beams are imaged on a grating 36, where they again combine into a common beam, leave the suppressor device 6, and are deflected onto a single detector. Instead of the grating, prisms can also be used.

Figure 13:
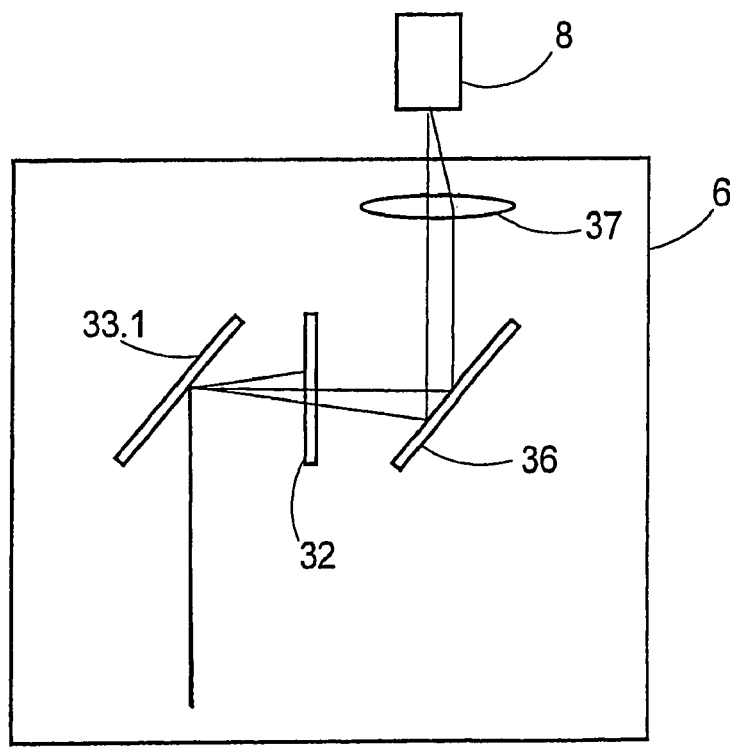
FIG. 13 is a schematic view of a third variant for the spectral selection.

The arrangement used in FIG. 13 is somewhat simpler compared to that in FIG. 12 and is based on the fact that for the detection, an exact overlap of the spectral parts is not important if the confocal filtering takes place before the blocking element. The spectrally-dispersed and transmitted fractions are imaged by the lens 37 directly onto the detector 8. Instead of a diaphragm array, a single diaphragm can also be used, which can, for instance, be embodied as a displaceable slit with variable width or as a simple edge, which is then driven by means of mechanical actuation to the known, and for blocking of the excitation spectrum necessary, position in the spectrum.

While the diaphragm array 32 can also function as the second selector 7 and can be used in the selection of the spectral ranges to be detected, in the case of the latter variant, it is additionally required. They can be arranged before or after the suppressor 6 and can consist of components similar to those in the first selector 2.

A variable bandpass filter is also suitable as an emission filter for single channel detectors. In this way, the transmission band is to be optimized for the emission spectrum of the fluorescence dye to be detected in the corresponding channel.

In the following, arrangements are described, which fulfill the functions necessary in the applications of a broadband emitting or variable broadband laser light source in an LSM through appropriate combination of the components described above.

Figure 14:
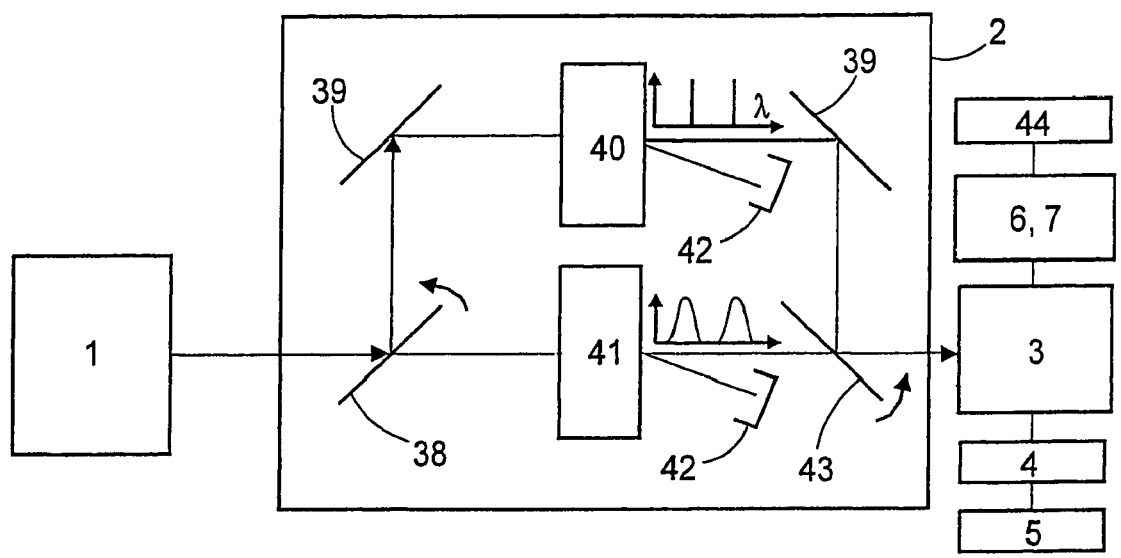
FIG. 14 is a schematic view of an arrangement for multiline excitation with selectable spectral width.

In FIG. 14, an arrangement is shown, with which a multi-line excitation with selectable spectral widths is possible. From an illumination source 1, which contains a variable broadband or broadband emitting laser, the light can be guided onto a narrowband AOTF 40 or a broadband AOTF 41 by means of a switchable mirror 38, and optionally through another mirror 39. The desired spectral width of the light used for the excitation of the fluorescence can be selected as indicated in the schematically shown transmission spectrum. If a broadband AOTF 41 is used, the bandwidth of the preferably pulsed laser is not cut off, so that multiphoton processes in the specimen are possible. The switchable mirror 38 can also optionally be a fixed neutral beam splitter, preferably with distribution ratio of 50:50. The same type of mirror 43 is used for re-combining the partial beams from both the channels. The combining of both the beams is also possible with the help of a polarizing optical splitter.

There is the additional possibility of realizing the above-mentioned function by using an acousto-optical component with switchable spectral width. In that case, the splitting and the combining of the beams are not necessary. The unutilized part of the beam as zeroth order diffraction of the respective AOTF's 40, 41 is deflected to a beam trap 42. On the other side, the selected beam is incident on the separators 3, which contain a variable or an achromatic main color splitter. The fluorescence signal generated after the interaction with the specimen 5 is guided through the second selector devices 7, which are designed as a variable bandpass emission filter and also fulfill the function as the suppressor device 6, to a single detector 44. With this arrangement, selection of at least two spectral ranges within the scope of the possibilities of AOTF 40, 41 is possible, whereby there is the possibility of the fast-action switching in and out, as well as of the intensity modulation or attenuation at the same time.

Figure 15:
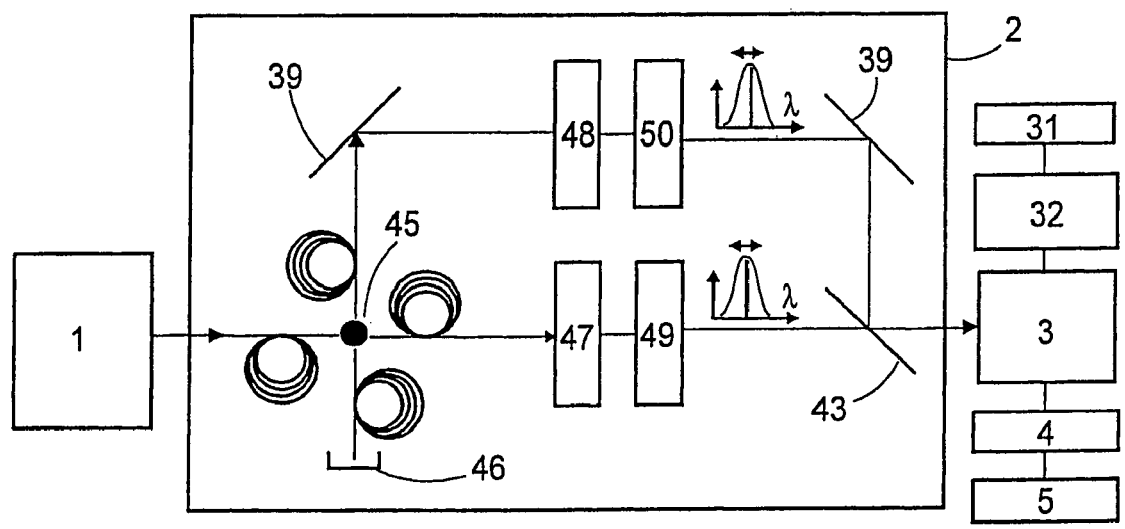
FIG. 15 is a schematic view of another arrangement for multiline excitation with variably adjustable spectral width.

In FIG. 15, an arrangement for multiline excitation with variably adjustable spectral width is shown. The laser light from the illumination source 1 is either transmitted through directly or is deflected by 90° by means of a fiber optic switch 45 based on piezoelectric actuation of the optical components for the deflection. The switch can, therefore, be tuned for a wavelength range from 450 to 700 nm, from 780 to 850 nm or from 1260 to 1650 nm. The response time lies in the range of milliseconds, so that a fast switching in and out of the two beams of light can be done, and additionally the beam can also be deflected onto a beam trap 46.

In both of the paths of the beams, two different configurable variable bandpasses 47, 48 are available, so that it is possible to select two spectral ranges with variable widths from the broadband laser beam. Since the fiber optical switch 45 can perform only the switching function, the functions of the intensity modulation, as well as attenuation, are each performed by components such as, for instance, filter wheels 49, 50, which are switched in down the beam path. The fiber optic switch 45 can also be substituted by a fast-acting switching mirror 38, or a fixed dichroic splitter, which can be embodied as a longpass or a shortpass filter, if the wavelength ranges are fixed. The selected beam is combined again into a single beam by means of a switchable mirror 43. Instead of the switchable mirror 43, a dichroic splitter, a neutral beam splitter or a polarizing optical splitter can also be employed. The beam falls on the separator 3, which can comprise, like before, a variable or an achromatic HFT. The fluorescence signal generated after the interaction with the specimen 5 is detected by the line detector 31. The suppressor 6 and the second selector 7 are realized by means of an individual spectrally sensitive diaphragm array 32.

Figure 16:
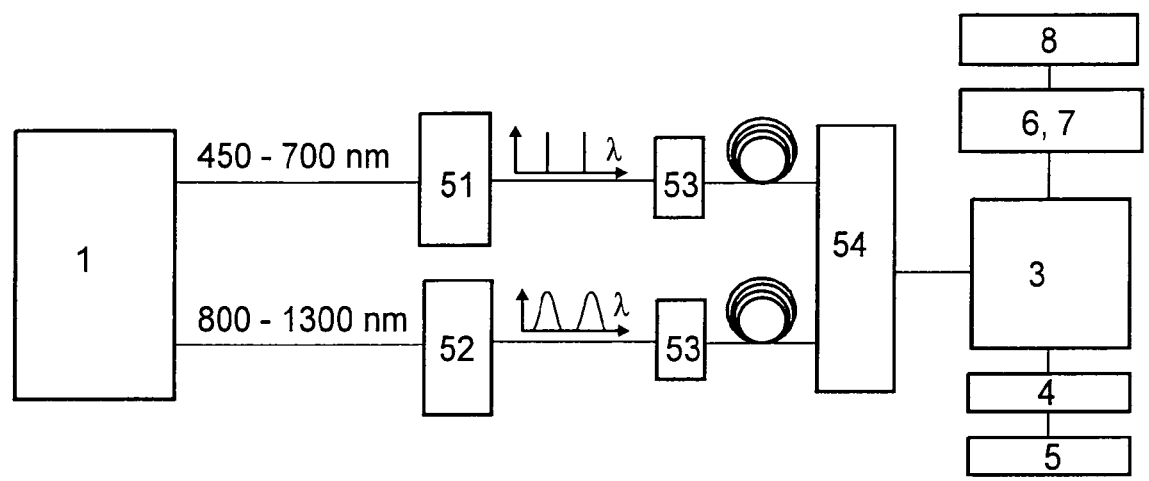
FIG. 16 is a schematic view of an arrangement for combination of tunable single-photon and multiphoton excitation.

Finally, an arrangement is shown in FIG. 16, in which single-photon or multiphoton excitations are possible optionally or in combination. This is of advantage especially in experimental methods, in which the specimen 5 is manipulated. From the illumination source 1, two broadband or variable broadband spectral ranges are available simultaneously. Suitable for that is the illumination unit shown in FIG. 5. In the example shown herein, the visible wavelength range from 450 to 700 nm and in the near-infrared wavelength range from 800 to 1300 nm are available. At least, the beam in the near-infrared region is present in the form of femtosecond pulses. Both the wavelength ranges can be tuned simultaneously in initially separate paths of the beams according to the requirements of the experiment. Thereby, in the visible spectral range, the selection of the wavelength is done preferably by means of a narrowband AOTF 51. In the near-infrared range, the wavelength range is selected preferably by means of an AOM 52. In contrast to the AOTF, the AOM 52 has the advantage that it does not cut off the spectral bandwidth of the femtosecond pulses. Using the beam in the near-infrared region, besides the multiphoton excitations, manipulation of the specimen 5 is also possible, whereby the visible spectral range primarily serves the purpose of normal imaging in the case of single-photon excitation.

In the case in which the beam in the visible spectral range is also present in the form of pulses, it is possible in principle to extend the path of the beam by one more branch, which is however not shown in FIG. 16. In this branching, through additional frequency doubling, beams in the wavelength range from 225 to 350 nm can be generated. One can thus obtain a beam in the ultraviolet range, with which certain manipulations, such as, for example, the so-called Uncaging, can be performed efficiently. Ideally, this frequency conversion of the spectral selection is done down the line in the beam path using an AOTF, so that only the already selected beam is doubled. In all the paths of the beams, a dispersion compensation unit 53, known in the prior art, is provided. Through this, the pulse length of a corresponding laser beam can be regulated. Due to the two separate paths of the beams for the selected spectral ranges, both the beams must be combined again by means of a beam combiner 54. According to the prior art, this beam combiner 54 can be realized on the basis of dichroic splitter layers.

The arrangement shown in FIG. 16 can also be combined with the arrangement shown in FIG. 14, so that on one hand both the mentioned wavelength ranges are available and on the other hand, there is the additional option of using a broadband AOTF with the already mentioned advantages of conservation of the energetic and spectral or temporal structure of the laser light in the case of the spectral range from 450 to 700 nm.

While using a laser scanning microscope, various biomedical applications are possible with the above described methods and apparatus, for which an optimization of the excitation wavelengths or wavelength ranges and the wavelengths or the wavelength ranges to be detected, play an important role.

Especially interesting applications for optimizing the excitation wavelength are the so-called Fluorescence Resonance Energy Transfer experiments (FRET experiments). In such experiments, only those dye combinations are used in which the emission wavelength of donor dye overlaps the excitation wavelength of the acceptor dye in a specific range. A cross excitation of both the dyes with the excitation wavelength of the donor dye should however be avoided as much as possible, since artifacts cannot be ruled out even with time consuming and elaborate checks and hence the results are less informative. Selection of an optimum excitation wave, that is, the most efficient one for the donor dye, without exciting the acceptor, is of considerable advantage, which increases the accuracy of the measurement accordingly and thus enables a user to obtain more precise information about the structure under investigation. In addition to that, the free selection of the excitation wavelength opens the possibility of achieving a separation of the cross excitation and FRET resulting from excitation with two or more neighboring lines and the corresponding calculated result of the obtained fluorescence images.

Another method, in which the optimization of the excitation wave can be employed, is the so-called Fluorescence Lifetime Imaging Microscopy (FLIM). Here, the half-life of the excited state of the dye in the living cell is measured, whereby the half-life lies in the nanosecond range. In this way, the half-life depends critically on the local environment of the specimen. An efficient excitation with avoidance of cross-excitation is essential for the exact determination of the half-life and its dependence on the local ambience. Such measurements can also be combined with FRET experiments.

Another application, in which the optimization of the excitation wavelength using broadband emitting or variable broadband lasers plays an important role, is the Fluorescence Correlation Spectroscopy (FCS). This case involves a very sensitive method, with which the bonding properties of the molecules within the confocal volume obtained from the LSM can be determined. Good tuning of the excitation wavelength for the dye is important in order to obtain an informative auto-correlation signal, and more than that for a good cross-correlation signal. This tuning makes it possible to use suitable dyes which were selected not according to the criterion "maximum excitation," but according to the criterion "minimum crosstalk." Minimization of the crosstalk, that is, minimization of the excitation of dyes with longer long waves by means of spectral offshoots of dyes with shorter short waves enables a more exact evaluation of the correlation signal, because the event to be measured is not falsified. With the possibility of tuning, other dyes can be explored, which are more suitable for the respective case of the application. This is of particular importance in cross correlations operating with at least two dyes.

The invention also offers advantages in the identification of dyes with the help of specific spectral information. With the free selection of the excitation wavelengths, it is often possible to evaluate the intensity difference of the signal with two or more discreet wavelengths in order to identify the signal of the dye. It is of advantage if the discreet wavelengths are thereby made available at the same time, because otherwise the tuning of the laser to another wavelength takes too long to be of use with living specimens. The wavelengths can be switched on alternatively in short sequences so that the fluorescence signal can be identified almost without delay. Thereby, the selectivity of the method results from the free selection of the wavelengths, due to which special characteristic signatures, taking into consideration the entirety of the dyes present in the specimen, can be used.

By using the multiphoton excitation in the range of 700 to 1000 nm, the method can also be used for strongly scattering specimens like tissue thick slices, tissue sections or whole animals, because the direct detection—the so-called non-descanned detection—can also be used. This enables, for example, the access to more complex measurements of ion concentrations in the tissue slices, because the signals can be registered with the necessary time resolution in the millisecond range and can be subsequently spectrally resolved at the same time. The speed of the measurement is not dependent on the speed for the tuning of the laser, but only on the speed of the scanner.

The method and the arrangement according to the invention are also suitable for the manipulation of the specimens. In general this means the excitation of fluorochromes with the aim of bleaching exactly to a point as a photochemical modification—for example uncaging, photo conversion or photo activation—or physical destruction. For example, both the wavelengths in the ultraviolet range as well as in the near infrared range are required for the uncaging. On the other hand, the image is taken in the visual range. Here also, in order to follow the process during the manipulation itself, one would like to work as simultaneously as possible. By optimizing the used wavelengths, both the uncaging as well as the excitation of the dye for the signal generation and thus the imaging can be optimized and the exposure of the specimen of can be minimized.

The applications described here represent only an exemplary selection. Though not explicitly mentioned here, the method according to the invention can also be used in other methods of examination that may be obvious to the user. It is to be understood that the present invention is not limited to the illustrated embodiments described herein. Modifications and variations of the above-described embodiments of the present invention are possible, as appreciated by those skilled in the art in light of the above teachings. It is therefore to be understood that, within the scope of the appended claims and their equivalents, the invention may be practiced otherwise than as specifically described.

What is claimed is:

1. A method for examining specimens through the use of a microscope, the method comprising the steps of:

generating spatially coherent light in at least one continuous wavelength range or a continuously tunable wavelength range for illumination of a specimen;

selecting one or more wavelengths or wavelength ranges of the illumination light in dependence on at least one of the specimen and a prespecified method of examination;

illuminating the specimen with the illumination light with the selected wavelengths or wavelength ranges;

separating the illumination light and the emission light radiated back by the specimen into different beam paths, based on the selected wavelengths or wavelength ranges;

suppressing the illumination light radiated back by the specimen, based on the selected wavelengths or wavelength ranges;

following suppressing of the illumination light radiated back by the specimen, detecting the emission light; and configuring the microscope according to a maximum value of a prespecified control variable R, wherein the control variable R is based on the mean intensity of the detected emission light coming from the sample;

wherein the selection of the wavelengths or the wavelength ranges of the illumination light is tuned with the separation of the detection light and the illumination light and the suppression of the illumination light in such a manner that the control variable R assumes the maximum value.

2. The method according to claim 1, wherein the microscope is a raster microscope, further comprising the step of sampling of the specimen using the raster microscope.

3. The method according to claim 1, further comprising the steps of:

marking the specimen with one or more dyes;

exciting the dyes to emit in response to the illumination light; and detecting the emitted light as the emission light.

4. The method according to claim 1, wherein the wavelengths or the ranges of the wavelengths of the emission light lie at least partially in the wavelength range of the illumination light.

5. The method according to claim 1, wherein for the tuning of the wavelengths or wavelength ranges of the illumination light, the wavelengths or wavelength ranges are varied in prespecified steps and for each prespecified step, at least one image is generated from the detected emission light and the control variable R is determined.

6. The method according to claim 5, further comprising the step of tuning with respect to the spectral ranges of the detected emission light, in which in each prespecified step, the variation of the wavelengths or wavelength ranges is done according to the tuning.

7. The method according to claim 1, wherein the detection takes place with spectral resolution.

8. The method according to claim 1, wherein the tuning is done on the basis of a reference specimen.

9. The method according to claim 1, wherein the tuning is done on the specimen itself.

10. The method according to claim 1, further comprising the step of:

selecting the wavelengths or the wavelength ranges of the illumination light, which are set at the beginning of the tuning, on the basis of a database.

11. The method according to claim 1, wherein the selection of (a) at least one of the wavelengths or the wavelength ranges of the illuminating light and (b) the spectral ranges of the emission light to be detected takes place automatically.

12. The method according to claim 1, wherein the selection of (a) at least one of the wavelengths or wavelength ranges of the illumination light and (b) the spectral ranges of the emission light to be detected takes place manually by a user.

13. The method according to claim 1, further comprising the steps of:

generating images from the detected emission light and using the sum of the mean intensities over the generated images in dependence on the wavelengths or wavelength ranges of the illumination light as the control variable R.

14. The method according to claim 1, further comprising the steps of:

generating images from the detected emission light and using the difference of the mean intensities of two or more spectral ranges in the images in dependence on the wavelengths or wavelength ranges of the illumination light as the control variable R.

15. The method according to claim 1, further comprising the steps of generating images from the detected emission light and using the difference between the mean intensities of first and second selected regions in the images in dependence on the wavelengths and wavelength ranges of the illumination light as the control variable R.

16. The method according to claim 15, wherein from a first of the two regions, the light to be detected is emitted, and from the second of the two regions, essentially interfering light is emitted.

17. The method according to claim 15, wherein, in the control variable R, the weighted and normalized intensity from the first region is taken into consideration.

* * * * *

UNITED STATES PATENT AND TRADEMARK OFFICE
CERTIFICATE OF CORRECTION

PATENT NO. : 7,593,158 B2 Page 1 of 1
APPLICATION NO. : 11/330384
DATED : September 22, 2009
INVENTOR(S) : Wilhelm et al.

It is certified that error appears in the above-identified patent and that said Letters Patent is hereby corrected as shown below:

Title page, item [73] assignee, change "Micro Imaging"

to --MicroImaging--

On the Title page,

[*] Notice: Subject to any disclaimer, the term of this patent is extended or adjusted under 35 USC 154(b) by 92 days Delete the phrase "by 92 days" and insert --by 345 days--

Signed and Sealed this

Twenty-seventh Day of July, 2010

David J. Kappos
*Director of the United States Patent and Trademark Office*